(12) United States Patent
Hendrickx et al.

(10) Patent No.: US 10,508,975 B2
(45) Date of Patent: Dec. 17, 2019

(54) SAMPLE COLLECTION DEVICE

(71) Applicant: ORION GENOMICS LLC, St. Louis, MO (US)

(72) Inventors: Jacob Paul Hendrickx, Campbell, MN (US); Michael Sylvester Botzet, Garfield, MN (US); Nathan D. Lakey, Chesterfield, MO (US); Anthony D. Favello, St. Louis, MO (US)

(73) Assignee: Orion Genomics LLC, St. Louis, MO (US)

( * ) Notice: Subject to any disclaimer, the term of this patent is extended or adjusted under 35 U.S.C. 154(b) by 126 days.

(21) Appl. No.: 15/579,299

(22) PCT Filed: Jun. 6, 2016

(86) PCT No.: PCT/US2016/036049
§ 371 (c)(1),
(2) Date: Apr. 25, 2018

(87) PCT Pub. No.: WO2016/197122
PCT Pub. Date: Dec. 8, 2016

(65) Prior Publication Data
US 2019/0195745 A1    Jun. 27, 2019

Related U.S. Application Data

(60) Provisional application No. 62/171,870, filed on Jun. 5, 2015, provisional application No. 62/237,492, filed on Oct. 5, 2015.

(51) Int. Cl.
*G01N 1/04* (2006.01)
*B65D 25/20* (2006.01)
(Continued)

(52) U.S. Cl.
CPC ............... *G01N 1/04* (2013.01); *B01L 3/545* (2013.01); *B65D 25/205* (2013.01);
(Continued)

(58) Field of Classification Search
CPC combination set(s) only.
See application file for complete search history.

(56) References Cited

U.S. PATENT DOCUMENTS 3,921,459 A * 11/1975 Willett ..................... G01N 1/04
73/864.41
4,927,605 A     5/1990 Dorn et al.
(Continued)

FOREIGN PATENT DOCUMENTS

| FR | 1545575 A | 11/1968 | |
| WO | 2004/063720 A1 | 7/2004 | |
| WO | WO-2004063720 A1 * | 7/2004 | ............... G01N 1/08 |

OTHER PUBLICATIONS

International Search Report and Written Opinion from PCT/US2016/036049 dated Oct. 6, 2016; 13 pages.

*Primary Examiner* — Nathaniel J Kolb
(74) *Attorney, Agent, or Firm* — Kilpatrick Townsend & Stockton LLP

(57) ABSTRACT

A sampling device having a lower portion with a sample container. A cap is moveably attached with the lower portion and includes a cutting edge configured for cutting a leaf. When the cap is attached to the lower portion with a leaf there between, a leaf sample is deposited into the sample container of the lower portion. The cap includes a vent in fluid communication with the sample container such that the leaf sample is dried. A detachable label can extend from the lower portion.

19 Claims, 14 Drawing Sheets

(51) Int. Cl.
  *B65D 73/02*   (2006.01)
  *B65D 51/16*   (2006.01)
  *G01N 1/28*    (2006.01)
  *G01N 35/10*   (2006.01)
  *B01L 3/00*    (2006.01)
  *G01N 33/00*   (2006.01)

(52) U.S. Cl.
  CPC .......... *B65D 51/1611* (2013.01); *B65D 73/02* (2013.01); *G01N 1/286* (2013.01); *G01N 35/10* (2013.01); *B01L 3/50855* (2013.01); *B01L 2200/0684* (2013.01); *B01L 2200/185* (2013.01); *B01L 2300/021* (2013.01); *B01L 2300/022* (2013.01); *B01L 2300/043* (2013.01); *B01L 2300/044* (2013.01); *B01L 2300/0672* (2013.01); *B01L 2300/08* (2013.01); *B01L 2300/0829* (2013.01); *B65D 2203/02* (2013.01); *B65D 2221/00* (2013.01); *G01N 33/0098* (2013.01); *G01N 2001/288* (2013.01); *G01N 2001/2873* (2013.01)

(56) References Cited

U.S. PATENT DOCUMENTS

| | | | |
|---|---|---|---|
| 8,689,649 B2 * | 4/2014 | Shoemaker | G01N 1/286 |
| | | | 73/864.41 |
| 2006/0057738 A1 | 3/2006 | Hall | |
| 2007/0021684 A1 * | 1/2007 | Brielmeier | A01K 11/003 |
| | | | 600/564 |
| 2007/0269341 A1 | 11/2007 | Halverson et al. | |
| 2009/0042180 A1 * | 2/2009 | Lafferty | G06Q 10/087 |
| | | | 435/4 |
| 2009/0139353 A1 * | 6/2009 | Kline | G01N 1/08 |
| | | | 73/864.45 |
| 2010/0059533 A1 | 3/2010 | Unger et al. | |
| 2010/0218621 A1 | 9/2010 | Chen et al. | |
| 2011/0091364 A1 | 4/2011 | Voit | |
| 2015/0260615 A1 * | 9/2015 | Turchi | G01N 1/04 |
| | | | 435/6.11 |

* cited by examiner

SAMPLE COLLECTION DEVICE

CROSS-REFERENCE TO RELATED APPLICATIONS

This application is a national stage entry of International Application No. PCT/US2016/036049, filed Jun. 6, 2016, which claims the benefit of U.S. Provisional Application No. 62/171,4870, filed Jun. 5, 2015, and U.S. Provisional Application No. 62/237,492, filed Oct. 5, 2015, all of which are incorporated by reference herein in their entireties.

BACKGROUND OF THE INVENTION

Devices and processes for sampling biological material, such as plant specimens, can be complex and expensive. To correlate test results accurately, many systems utilize expensive and complex computer based GPS tracking methods, which include barcode reading, GPS tracking, and/or electronic sampling, and accordingly require highly trained personnel, who may not be available in all regions.

BRIEF SUMMARY OF THE INVENTION

Embodiments of the invention can be related to a sampling device and associated methods for use. Each sampling device can include a lower portion, a cap, and an attached label. The lower portion can contain a sample container. The cap can include a cutting post and be configured to attach to the lower portion while simultaneously cutting a sample there between.

The sample can be a biological sample, such as plant matter, and more specifically a leaf, and the sampling device can be specifically constructed only for use with plant matter, such as a leaf. For example, the cutting post of the cap can be constructed from a polymer which would be unsuitable for other biological materials (e.g. skin, fat) by not having a sharp enough cutting edge. In addition, the cap can be fluidly vented in order to dry vegetable matter samples after procurement and provide a channel to add testing fluid during processing. Such a vent may be incompatible with other types of biological matter, such as animal tissue, because it would not prevent the ingress of bacteria and other matter.

Many embodiments of the invention are related to sampling device. The sampling device can include a lower portion with a sample container. A cap can be moveably attached with the lower portion and include a cutting edge configured for cutting a leaf. When the cap is attached to the lower portion with a leaf there between, a leaf sample is deposited into the sample container of the lower portion. The cap can include a vent in fluid communication with the sample container such that the leaf sample is dried. A detachable label can extend from the lower portion.

Many embodiments of the invention are related to a sampling device system. The system can include a plurality of rigid labels detachably connected to each other in a side by side formation. Each rigid label can be elongated from a back portion to a front portion. Each front portion can be detachably connected to a sampling device. The system may include a shipping box for holding the plurality of rigid labels, a shipping bag for holding the sampling devices detached from rigid labels, and/or a desiccant for use within the shipping bag to dry out the leaf samples contained within each sampling device.

Many embodiments of the invention are related to method for sampling a leaf of a plant using a sampling device system. A strip may be obtained that includes a plurality of rigid labels detachably connected to each other in a side by side formation. One rigid label can be detached from the plurality of labels and interconnected sampling device from the strip. The one rigid label can be detached from its sampling device and associating the one rigid label with a particular plant. A particular leaf sample of particular plant can be obtained by positioning a particular leaf of the particular plant between the cap and bottom portion attaching the cap to the bottom portion. The sampling device holding the particular leaf sample can be placed within a shipping container having a desiccant for drying out the particular leaf sample. The shipping container holding the sampling device and particular leaf sample can then be sent to a sample analysis facility.

Many embodiments of the invention are related to a method for analyzing a leaf sample of a plant. A shipping container holding at least one sampling device with a particular leaf sample stored therein can be received. The at least one sampling device can be removed from the shipping container and recording a particular code stored on the sampling device. The at least one sampling device can be filled with a sample preparation treatment fluid without opening the at least one sampling device by providing the sample preparation treatment fluid through a vent of the cap of the sampling device. At least some of a resultant fluid comprising the sample preparation treatment fluid and particular leaf sample can then be retrieved. An assay may be performed using the resultant fluid. Results of the assay may be associated with a particular plant using the particular code of the sampling device.

Many embodiments of the invention are related to a sampling device having a lower portion having a sample container and an elongated bore adjacent to the sample container. A cap can be moveably attached with the lower portion and comprising a cutting edge configured for cutting a leaf, such that when the cap is attached to the lower portion with a leaf therebetween, a leaf sample is deposited into the sample container of the lower portion, the cap also comprising a dead space passage configured to receive a first pipette. The cap can include a vent in fluid communication with the sample container such that the leaf sample is dried during transport of the sampling device, the vent being configured to receive a second pipette.

Many embodiments of the invention are related a method for sampling a leaf of a plant using a sampling device system. In the method, a plurality of sampling devices can be obtained, each sampling device comprising a dead space passage configured to receive a first pipette and a vent configured to receive a second pipette, the vent being in fluid communication with a sample container. The plurality of sampling devices can be arranged in first and second sampling device arrays. The plurality of sampling devices can be positioned adjacent to an array of pipettes, the array of pipettes comprising a first plurality of pipettes and a second plurality of pipettes arranged in alternating rows. The array of pipettes can be moved such that the first plurality of pipettes move into the vents of the first sampling device array and the second plurality of pipettes lower into the dead space passages of the first sampling device array. Fluid can be withdrawn from the vents of the first sampling device array using the first plurality of pipettes. The array of pipettes can be moved such that the first plurality of pipettes moving into the dead space passages of the second sampling device array and the second plurality of pipettes lower into the vents of the second sampling device array. Fluid can then be withdrawn from the vents of the second sampling device array using the second plurality of pipettes.

In many embodiments, the lower portion can include at least a partially cylindrical sample container.

In many embodiments, the lower portion can include a at least a partially round sample container.

In many embodiments, the lower portion can include an at least partially oval shaped sample container.

In many embodiments, the lower portion can be moveably attached to the cap by a flexible hinge.

In many embodiments, the lower portion can be moveably attached to the cap by an elongated post extending out of the cap.

In many embodiments, the elongated post can be slidable within an elongated cavity adjacent to the sample container within the lower portion.

In many embodiments, the cap can include an elongated cutting post that extends into the sample container.

In many embodiments, the elongated cutting post can be configured to immobilize the leaf sample at a bottom portion of the sample container.

In many embodiments, the bottom portion and cap can be configured to cut only the edge of a leaf.

In many embodiments, the bottom portion can include a depth limiting wall for limiting ingress of the bottom portion over a leaf.

In many embodiments, the label can be rigid and extend in cantilever from the lower portion.

In many embodiments, one of the cap and bottom portion can include a unique code that is correlated to the label.

In many embodiments, the vent can be adapted to act as a filling conduit for a sample preparation fluid.

BRIEF DESCRIPTION OF THE DRAWINGS

FIGS. 7A, 7B, 7C and 8 depict methods for using a sampling device, according to many embodiments of the invention.

DETAILED DESCRIPTION OF THE INVENTION

Specific examples are described below in reference to the provided figures. However, these examples are non-exclusive and non-exhaustive in order to provide a clear and concise disclosure. Thus, it should be understood that the examples are not limited to the particular combination of elements, and specific elements of the examples can be combined with the elements of other examples. In addition, each example does not depict a minimum combination of elements, and hence specific elements of the examples can be removed.

Figure 1A:
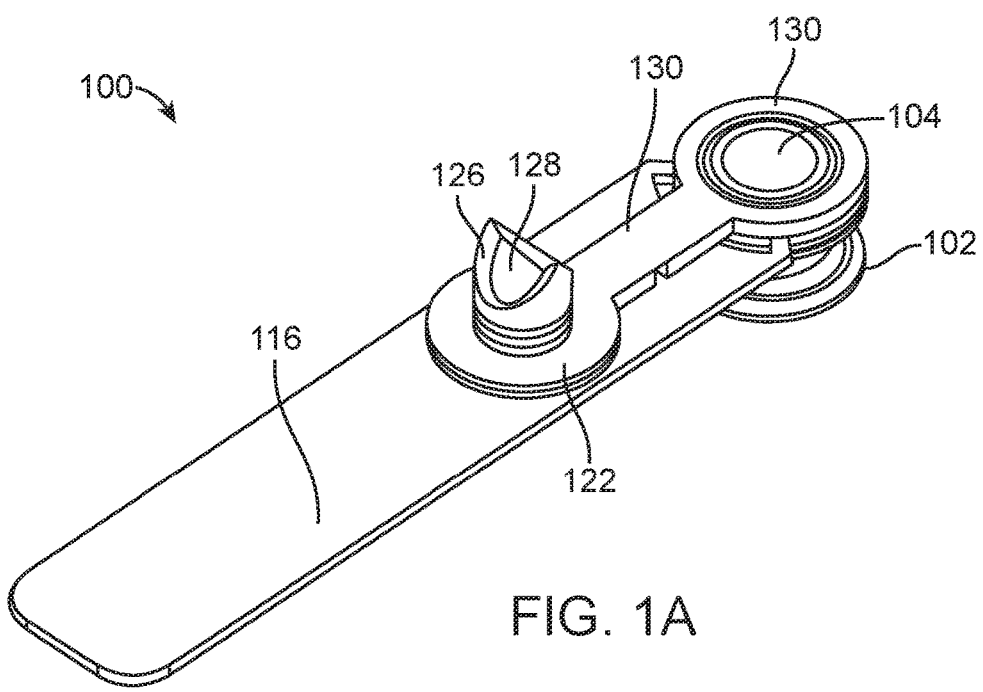
FIGS. 1A-1C respectively show perspective, top, and side views of a sampling device, according to many embodiments of the invention.
Figure 1B:
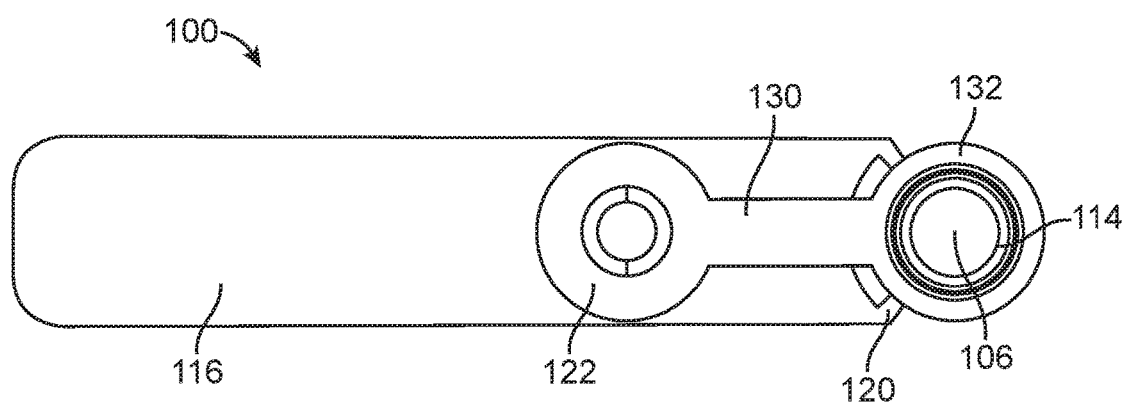
Figure 1C:
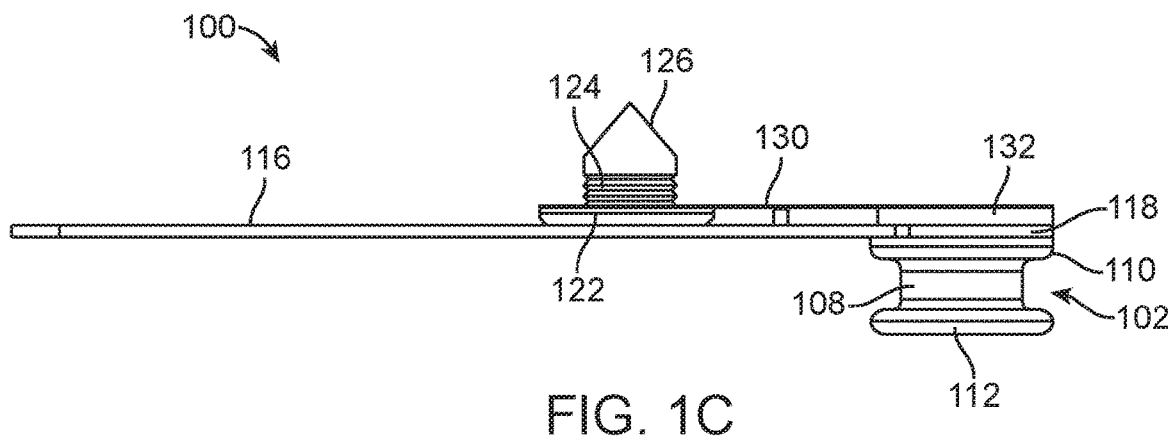

FIGS. 1A-1C respectively show perspective, top, and side views of a sampling device 100. The sampling device 100 can be constructed from a polymer, for example, polypropylene (PP), acrylonitrile butadiene styrene (ABS), or high density polyethylene (HDPE). The sampling device 100 includes a lower portion 102, which is configured to include an interior surface that defines a sample container. In this example, the interior surface is defined by a cylindrical wall 104 leading to a bottom surface 106. However, other shapes are possible.

The exterior of the lower portion 102 is cylindrical and includes a mid-section 108 having a relatively reduced diameter, which can be used for retaining the sampling device to tools and fixtures. A middle flange 110 and lower flange 112 flank the mid-section 108, and a cylindrical section 114 leads upwardly from the middle flange 110.

An elongated label 116 extends in cantilever from the lower portion 102, however, the elongated label 116 can extend from any portion of the sampling device 100. The label can be constructed from a rigid material (e.g. UV stabilized HDPE, UV stabilized PP, or polyvinyl chloride (PVC)), such that the label can support its own weight and that of the rest of the sampling device without deforming. The elongated label 116 can carry a variety of information, such as a serial number and product identification, in the form of barcodes, printed lettering, and/or electronic identifiers (e.g. radiofrequency identification (RFID) chip). Any portion of the sampling device 100 from which the elongated label 116 detaches from, including non-detached portions of the elongated label 116, can include an identification (e.g. bar code) that correlates the detached label to the remaining sampling device, and therefore correlates the detached label to any sample contained therein. A proximal portion 118 of the label 116 includes a circular opening so that the label 116 fits over and is supported by the cylindrical section 114 while abutting the middle flange 110 of the lower portion 102. The proximal portion 118 also includes thinned sections 120 that preferably fracture upon application of force to the elongated label 116. The lower portion 102 can be molded about the elongated label 116 to advantageously reduce production steps and cost.

The sampling device 100 also includes a cap 122 having an elongated cutting post 124 sized to fit within the cylindrical wall 104 of the lower portion 102. There can be little to no clearance between the elongated cutting post 124 and the cylindrical wall 104, such that the elongated cutting post 124 fits tightly within the cylindrical wall 104. The elongated cutting post 124 can be grooved as shown to reduce friction during insertion. In addition, the elongated cutting post 124 can include angular cutting edges 126 configured for cutting material, such as a plant specimen (e.g. leaves, bark, stalk, flowers, roots etc.). The elongated cutting post 124 can be of a length such that any vegetable matter cut by the cutting edges is physically trapped between the elongated cutting post and the bottom surface 106 of the lower portion 102. The cap 122 is fluidly vented by a passage 128 through extends through the elongated cutting post 124. While a circular shaped elongated cutting post 124 and cylindrical wall 104 are shown for use with the sampling device 100, other shapes are possible, including for example, fully or at least partially circle or oval (such as a D-shape), rectangular, polygonal, and semi-circular.

A tether 130 extends from the cap 122 to a circular portion 132 that connects to the cylindrical section 114 of the bottom portion 118. The tether 130 can be notched to preferably bend at a certain location along its length.

Figure 2A:
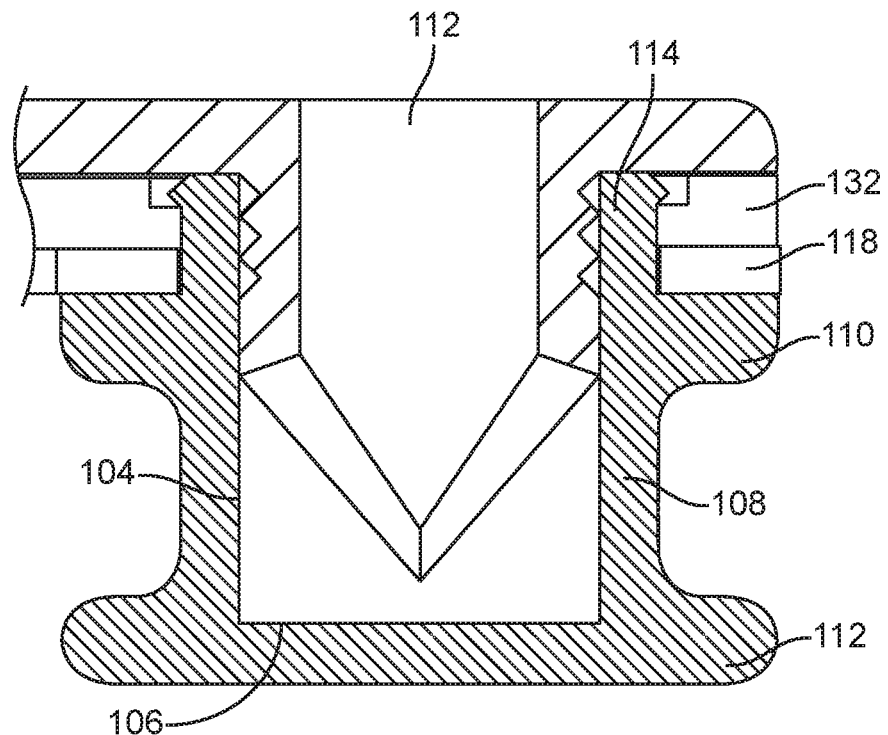
FIG. 2A shows a partial cross-sectional view of a sampling device, according to many embodiments of the invention.

FIG. 2A shows a partial cross-sectional view of the sampling device 100, with the cap 122 fitted to the lower portion 102. As shown, the cap 122 has been fitted by bending and/or fracturing the tether 130 and fitting the elongated cutting post 124 and the cylindrical wall 104. As a result, the cap 122 is securely held by the lower portion 102, and any matter that was cut by the cap 122 during this process is physically detained between the end of the elongated cutting post 124 and the bottom surface 106.

Figure 2B:
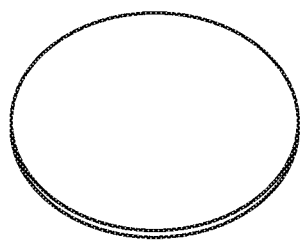
FIG. 2B shows a sample obtained by use of a sampling device, according to many embodiments of the invention.

The resulting cut matter will form a circular biscuit as shown at FIG. 2B, which will be secured from movement by the elongated cutting post 124. During transportation, a sample of vegetable matter may dry to the extent of becoming brittle. Thus, retaining the sample by the elongated cutting post 124 can help prevent the fragile sample from being easily dislodged and damaged. Notably, the bottom surface 106 remains in fluid communication to exterior surroundings by way of the passage 128 that passes through the cap 122. Hence, any biological matter stored within the sampling device 100 can be hydrated or dehydrated through passage of fluids through the passage 128.

Figure 3:
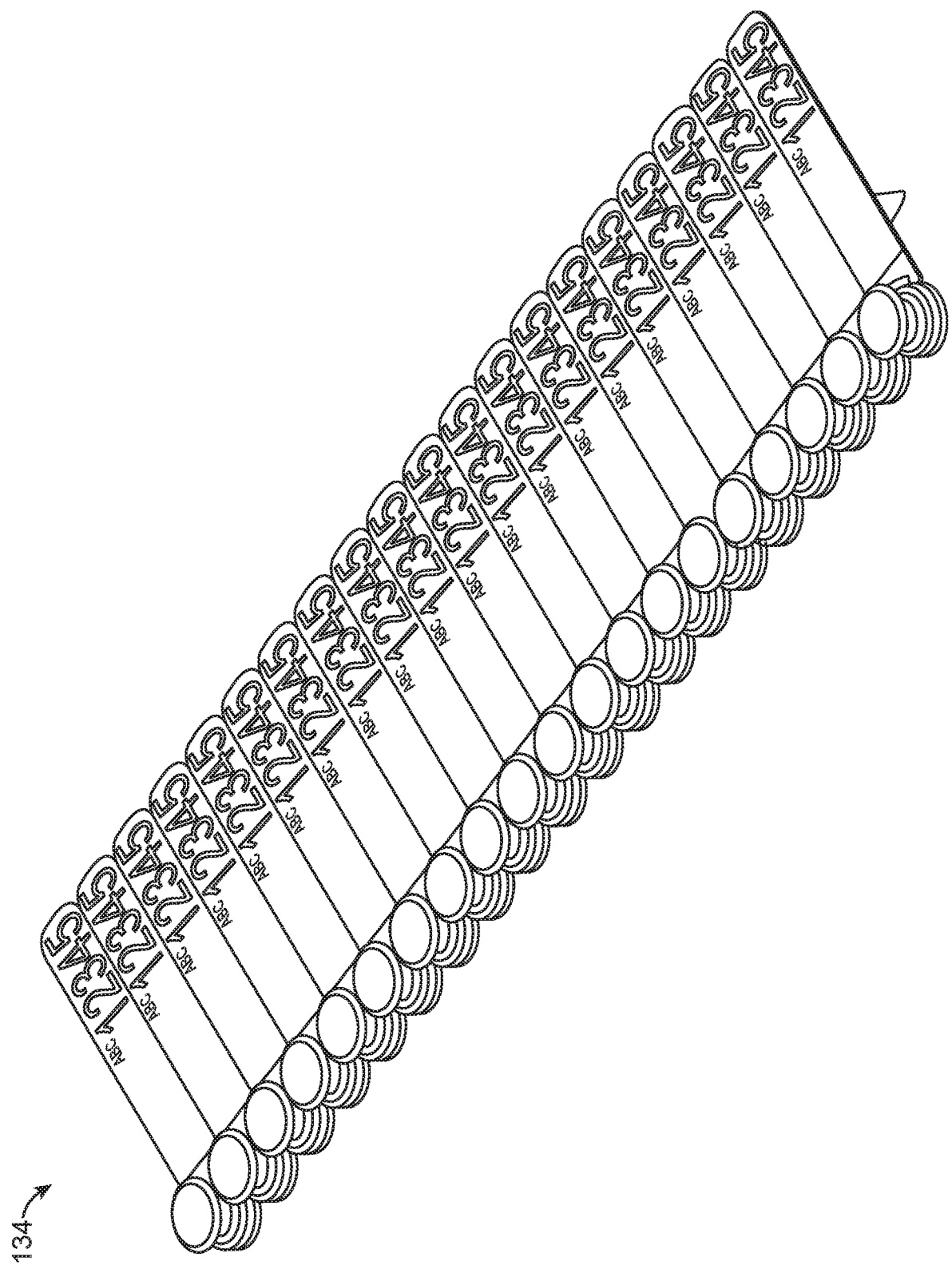
FIG. 3 shows a plurality of sampling devices, according to many embodiments of the invention.

FIG. 3 shows a plurality of sampling devices 134 arranged in a side by side format. Here, the labels 116 are formed as a strip and configured to forcibly detach from one another, for example, by applying force to perforated, notched, or thinned boundaries present between each label 116. The caps 122 and lower portions 102 of attached to each label, however are not attached to adjacent caps 122 and lower portions 102. Hence, detachment of a particular label 116 results in procurement of an individual sampling device 134.

Figure 4A:
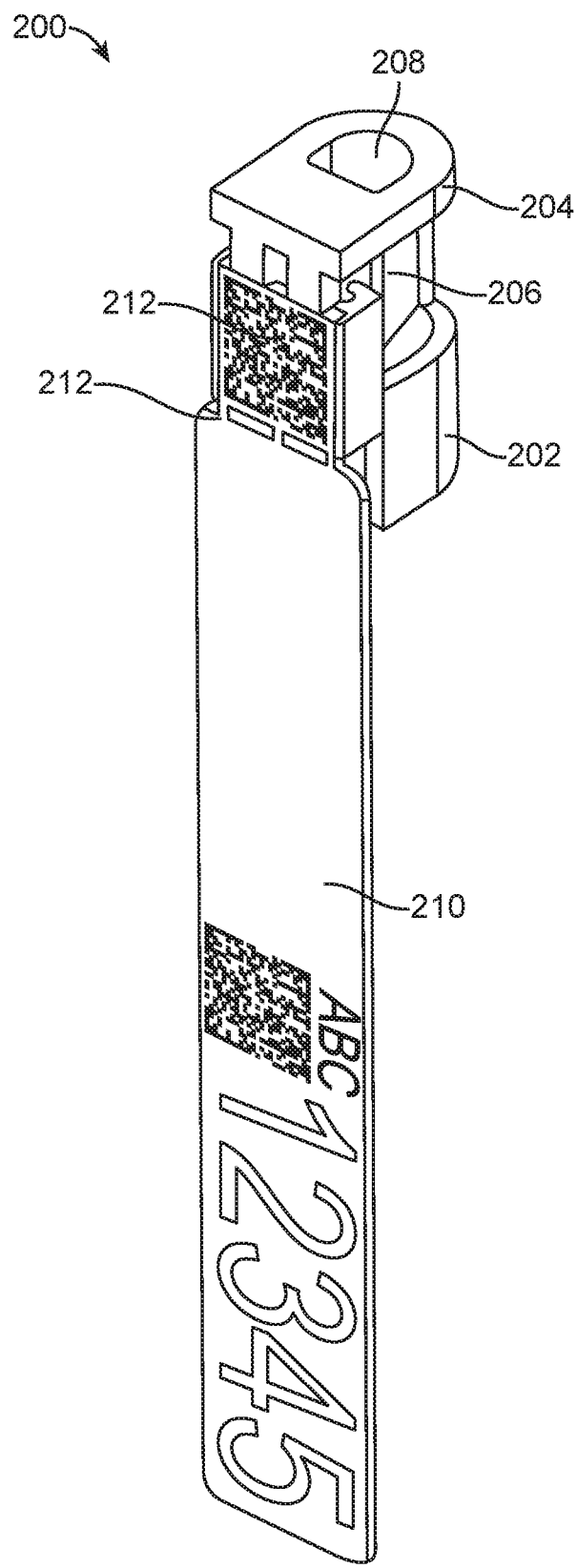
FIGS. 4A, 4B, and 4C respectively show perspective, top, and side views of a sampling device, according to many embodiments of the invention.
Figure 4B:
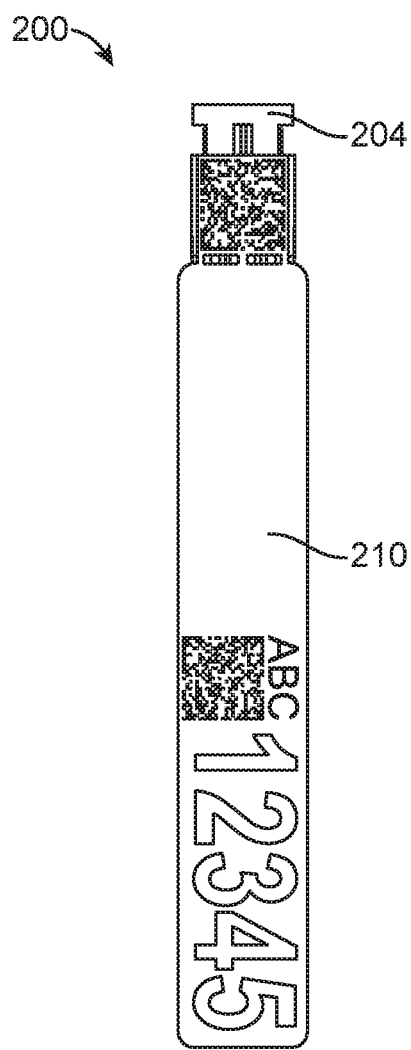
Figure 4C:
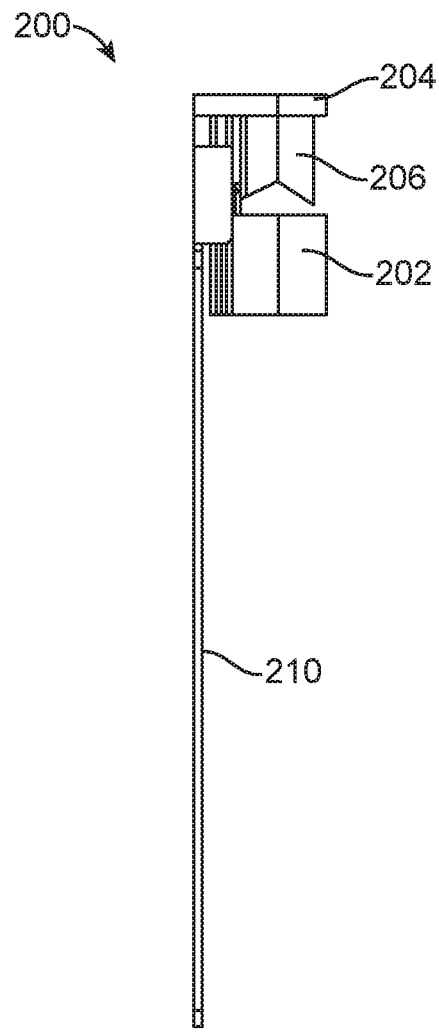

FIGS. 4A, 4B, and 4C respectively show perspective, top, and side views of another example of a sampling device 200, which shares many of the general features of the sampling device 100 shown at FIG. 1A. However here, the sampling device 200 includes a lower portion 202 having an interior container with a semi-circular "D-shaped" cross-section, instead of the circular cross-section of the sampling device 100 shown at FIG. 1A.

The sampling device 200 includes a cap 204 that includes an elongated cutting post 206 having a complimentary D-shaped cross-section cutting edge. There can be little to no clearance between the elongated cutting post 206 and the interior container of the lower portion 202, such that the elongated cutting post 206 fits tightly therein. The elongated cutting post 206 includes an interior passage 208 that fluidly vents the cap 204 and lower portion 202.

An elongated label 210 extends in cantilever from the lower portion 202. The label can be constructed from a rigid material (e.g. rigid polymer), such that the label can support its own weight and that of the rest of the sampling device without deforming. The elongated label 202 can carry a variety of information, such as a serial number and product identification, in the form of barcodes, printed lettering, and/or electronic identifiers (e.g. radiofrequency identification (RFID) chip). Any portion of the sampling device 200 from which the elongated label 210 detaches from, including non-detached portions of the elongated label 210, can include an identification (e.g. bar code) that correlates the detached label to the remaining sampling device, and therefore correlates the detached label to any sample contained therein. A proximal portion 212 of the elongated label 210 is secured to a portion of the cap 204, however, the proximal portion 212 can be secured to any portion of the sampling device. The proximal portion 212 also includes thinned sections 214 that preferably fracture upon application of force to the elongated label 210. The cap 204 can be molded about the elongated label 210 to advantageously reduce production steps and cost.

Figure 5A:
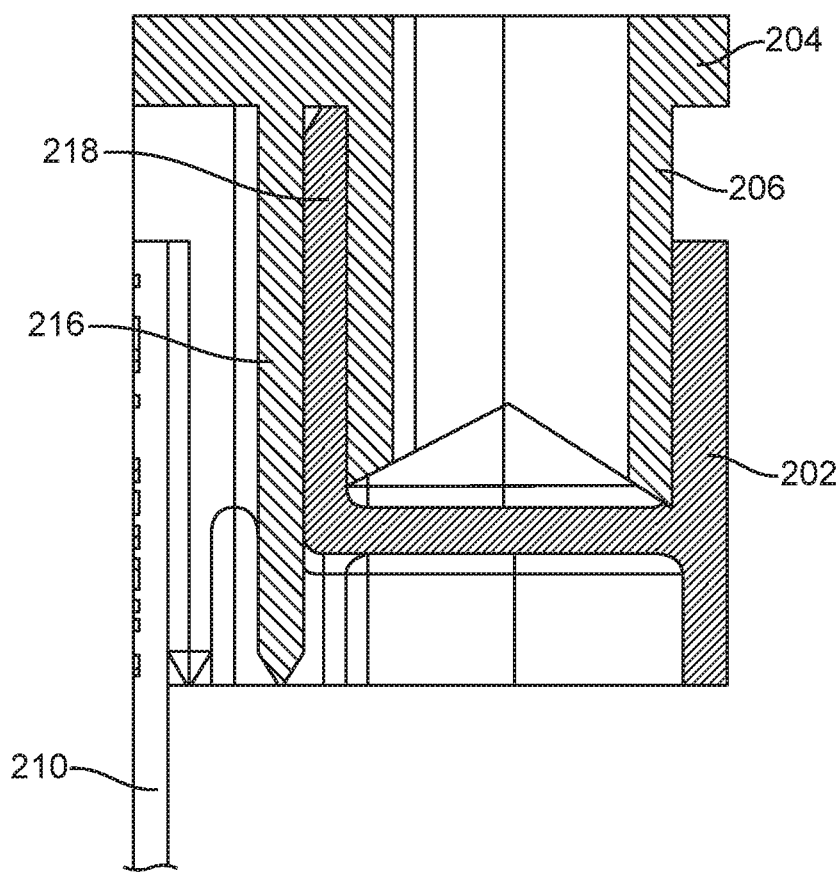
FIG. 5A shows a partial cross-sectional view of a sampling device, according to many embodiments of the invention.
Figure 5B:
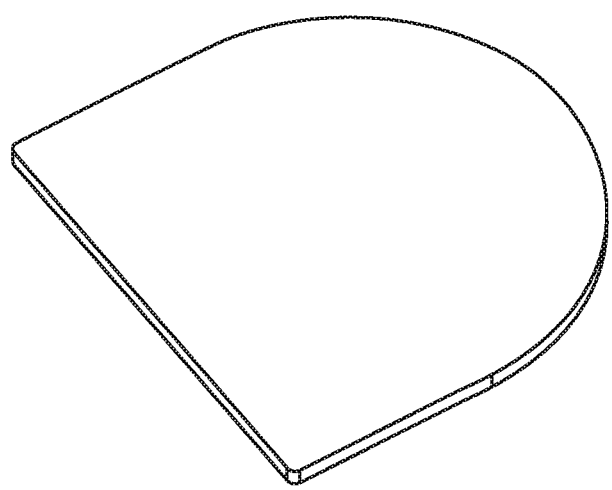
FIG. 5B shows a sample obtained by use of a sampling device, according to many embodiments of the invention.
Figure 5D:
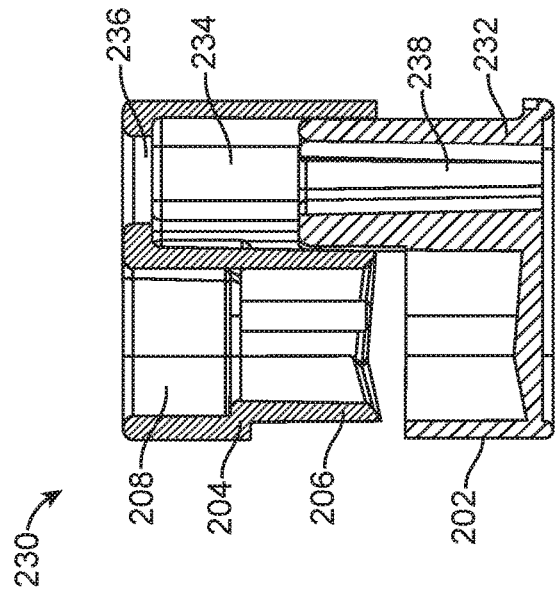
FIGS. 5C-5F show cross-sectional and top views of a sampling device, according to many embodiments of the invention.
Figure 5C:
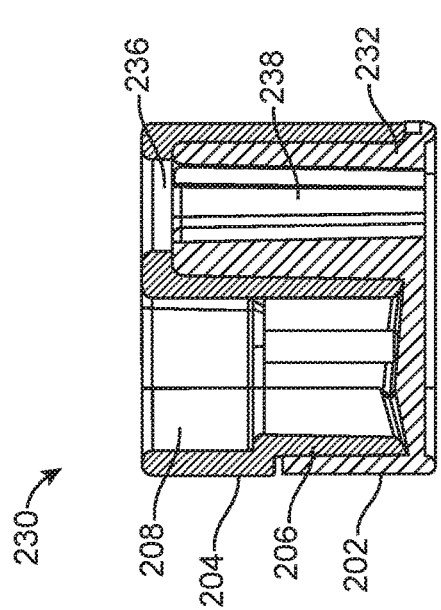

FIG. 5A shows a partial cross-sectional view of the sampling device 200, with the cap 204 fitted to the lower portion 202. As shown, the cap 204 has been fitted by sliding the cap downward onto the lower portion 202. A lateral post 216 cooperates with a passage within the lower portion 202 to serve as a travel guide for this operation. As a result, the cap 204 is securely held by the lower portion 202, and any matter that was cut by the cap 202 during this process is physically detained between the end of the elongated cutting post 206 and the bottom of the container within the lower portion 202. The resulting cut matter will form a D-shaped biscuit as shown at FIG. 5B, which will be secured from movement by the elongated cutting post 206. During transportation, a sample of vegetable matter may dry to the extent of becoming brittle. Thus, retaining the sample by the elongated cutting post 206 can help prevent the fragile sample from being easily dislodged and damaged. Notably, the lower portion 202 remains in fluid communication to exterior surroundings by way of the interior passage 208 that passes through the cap 204. Hence, any biological matter stored within the sampling device 200 can be hydrated or dehydrated through passage of fluids through the interior passage 208.

One particular advantage of the sampling device 200 is the ability to remove samples from an edge of a biological material, such as a leaf. This prevents the need to cut into or tear the biological material or disassemble the sampling device to retrieve a sample that was taken at a central portion of a leaf for example. A depth limiting wall 218 shown at FIG. 5A, prevents the ingress of the sampling device from protruding beyond an edge a leaf. Such a depth limiting feature is not limited to use with the sampling device 200 shown at FIG. 5A, and can for example be used with the sampling device 200 shown at FIG. 1A. While a partially circular/oval D-shaped elongated cutting post 206 and corresponding container of the lower portion 202 is shown for use with the sampling device 200, other shapes are possible, including triangular, fully oval, rectangular, polygonal, and circular.

FIGS. 5C-5F shows views of an alternative construction of the sampling device 230, which shares many of the same features as the sampling device shown at FIGS. 4A-4C. Hence, many of the same reference numbers are described above, and not repeated here for the sake of brevity. Here, a difference is that a lateral post 232 extends from the lower portion 202. The lateral post 232 cooperates with a shaft 234 of the cap 204. The cap 204 includes a dead space opening 236 that is open to a dead space passage 238 that extends through the lateral post 232. The dead space opening 236 is sized to allow a pipette to pass through into the dead space passage 238. Because there is only one sample container per sampling device 230, only the interior passages 208 hold samples, while the dead space openings 236 serve as passages into dead space. This is to provide compatibility with a standardized liquid handling machine, which provides a fixed pipette for each standardized well location. If the dead space openings 236 were not present, pipettes would otherwise collide due to the overall footprint of the sampling device 232, which is greater than the distance between two wells of a standard microplate.

Figure 5F:
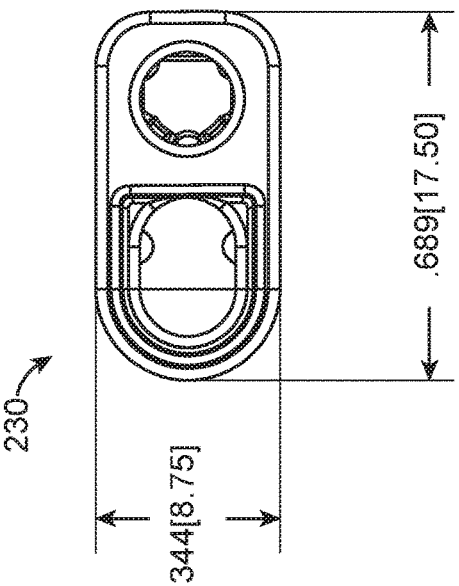
Figure 5E:
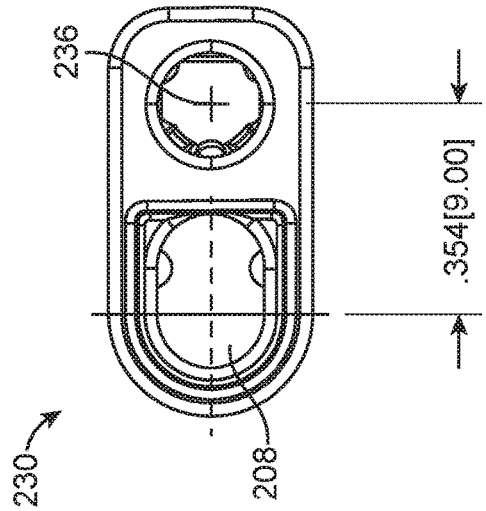
Figure 5G:
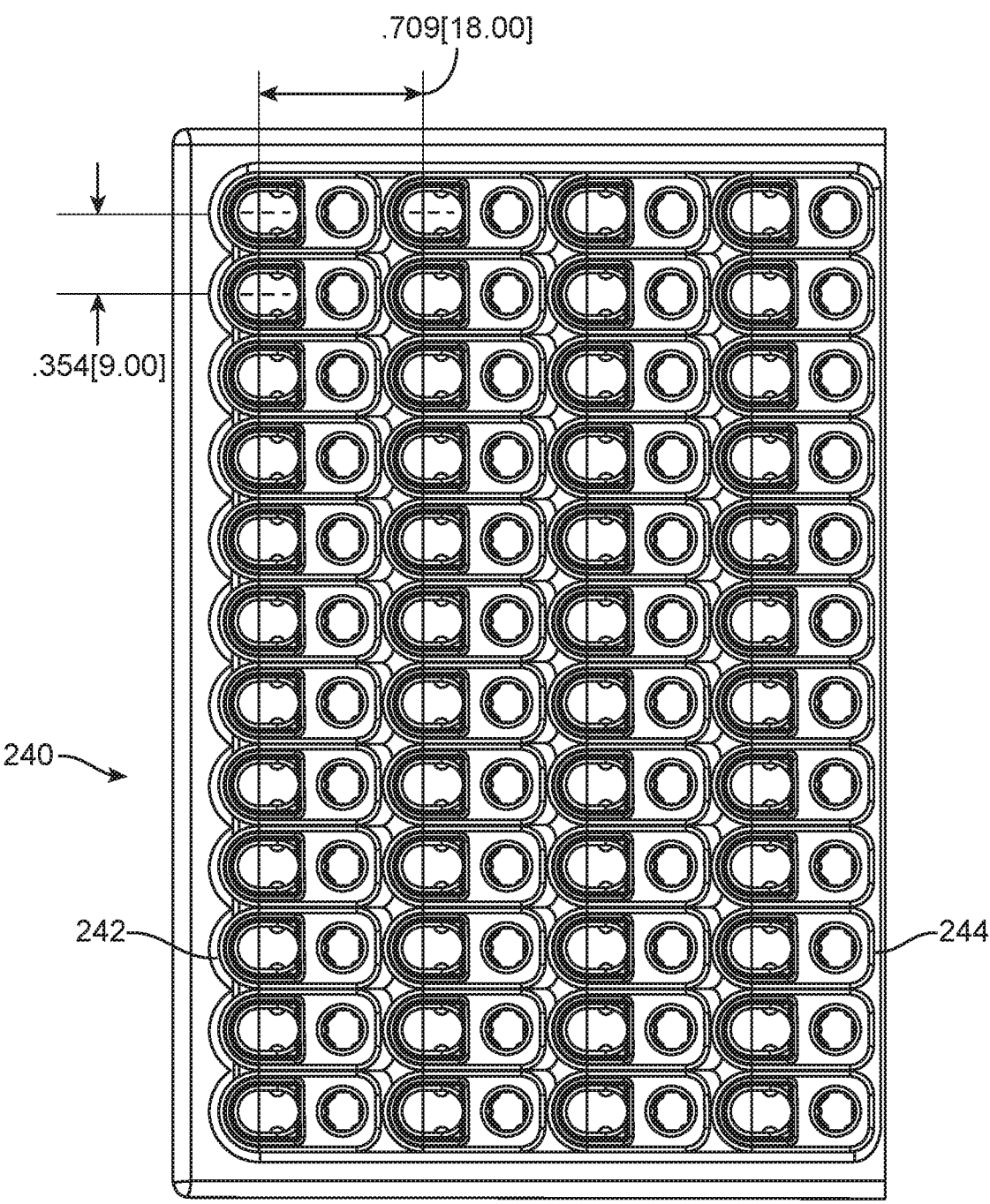
FIG. 5G shows a top view of an array of sampling devices, according to many embodiments of the invention.

The top views shown at FIGS. 5E and 5F show exemplary dimensions for the sampling device 230. Here, the center to center exemplary dimension between the interior passage 208 and the dead space opening 236 is 9 mm (0.354 in.). Further, the width of the sampling device 230 is 8.75 mm (0.344 in), which is less than the 9 mm spacing that is standard in micro-titer format and which enables the arrangement of a plurality of sample collection devices in a side-by-side array at 9 mm formatting; and the length is 17.5 mm (0.689 in), which is less than 18 mm (or two times the 9 mm spacing that is standard in micro-titer format) and which enables the arrangement of a plurality of sample collection devices in a side-by-side array at 2×9 mm formatting; and hence the interior passage 208 and the dead space opening 236 of the sampling device will be situated 9 mm apart in the X or Y direction from any abutting sampling device. These dimensions are based on compatibility with standardized microplate dimensions per Standards ANSUSLAS 1-2004 through ANSUSLAS 4-2004. Hence, 2, 4, 8, 12, 16, 24, 32 or ideally 48 sampling devices 230 can be arranged in an array as shown at FIG. 5G using a specialized tray 240, such that each interior passage 208 and opening 236 are placed at the theoretical well locations of a standardized 96 well microplate, and therefore arranged to be compatible with commercially available liquid robotic handling apparatuses configured for standardized microplates. The tray 240 includes curved portions 242 for fitting curved ends of the sampling devices 230, as well as a truncated side 244 that lines up with flat ends of the sampling devices 230. In this manner, two trays 240 can be arranged near each other such that the same multi-channel pipetting device can access both arrays to transfer samples efficiently to a second microtiter format plate, and in some embodiments, the two trays can be side by side to comprise for example, 96 sampling devices 230, as further discussed below.

Useful arrays of the invention are arranged at predetermined spacing. Exemplary useful spacing between sample collection devices in an array is the quotient of 9 mm and X where X is an integer, or optionally the product of 9 mm and X where X is an integer. Therefore a useful array would include center to center spacing of sample collection devices of 1.125 mm (9 mm/8), 2.25 mm (9 mm/4), 4.5 mm (9 mm/2), 9 mm (9 mm/1), 18 mm (9 mm×2), 27 mm (9 mm×3), 36 mm (9 mm×4), and 45 mm (9 mm×5) and beyond (9 mm×X). The number of sample collection devices can be as few as two, four, 8, 12, 16, 24, 36, 48, 96, 384, 768 and as many as 1,536 or more. An ordered array of sample collection devices can be one dimensional, where the devices are arranged in a row with even center-to-center spacing, and where a one dimensional multichannel pipette can simultaneously access two or more samples in the row. Optionally, a useful ordered array of sample collection devices in the invention can be two dimensional, where the devices are arranged in rows and columns with even center-to-center spacing in the rows and columns, and where a one dimensional multichannel pipette can simultaneously access two or more samples in a given row, or a given column, or optional where a two dimensional multichannel pipette can simultaneously access multiple samples in more than one row and more than one column. One embodiment of the invention is where sample collection devices have the same center-to-center spacing in rows that is different form the center to center spacing in columns. For example, the center to center spacing in rows is set at 9 mm, and in columns is set at 18 mm. Another embodiment of the invention is where sample collection devices have the same center-to-center spacing in rows that is the same as the center-to-center spacing in columns. For example, the center to center spacing in rows and columns is set at 9 mm.

Figure 6:
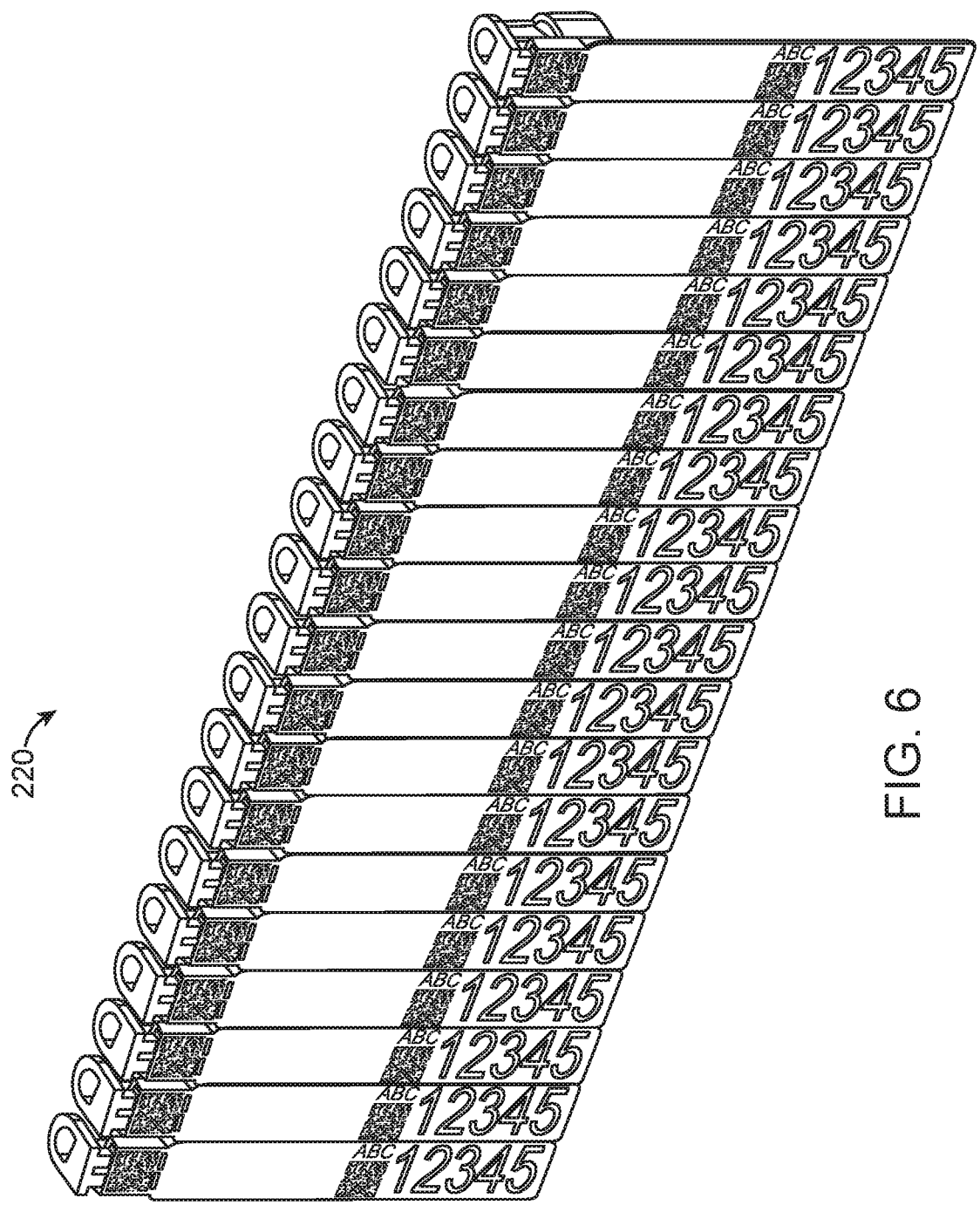
FIG. 6 shows a plurality of sampling devices, according to many embodiments of the invention.

FIG. 6 shows a plurality of sampling devices 220 arranged in a side-by-side format. Here, the labels 210 are formed as a strip and configured to forcibly detach from one another, for example, by applying force to perforated, notched, or thinned boundaries present between each label 210. The caps 204 and lower portions 202 of attached to each label, however are not attached to adjacent caps 204 and lower portions 204. Hence, detachment of a particular label 210 results in procurement of an individual sampling device 200.

Figure 7A:
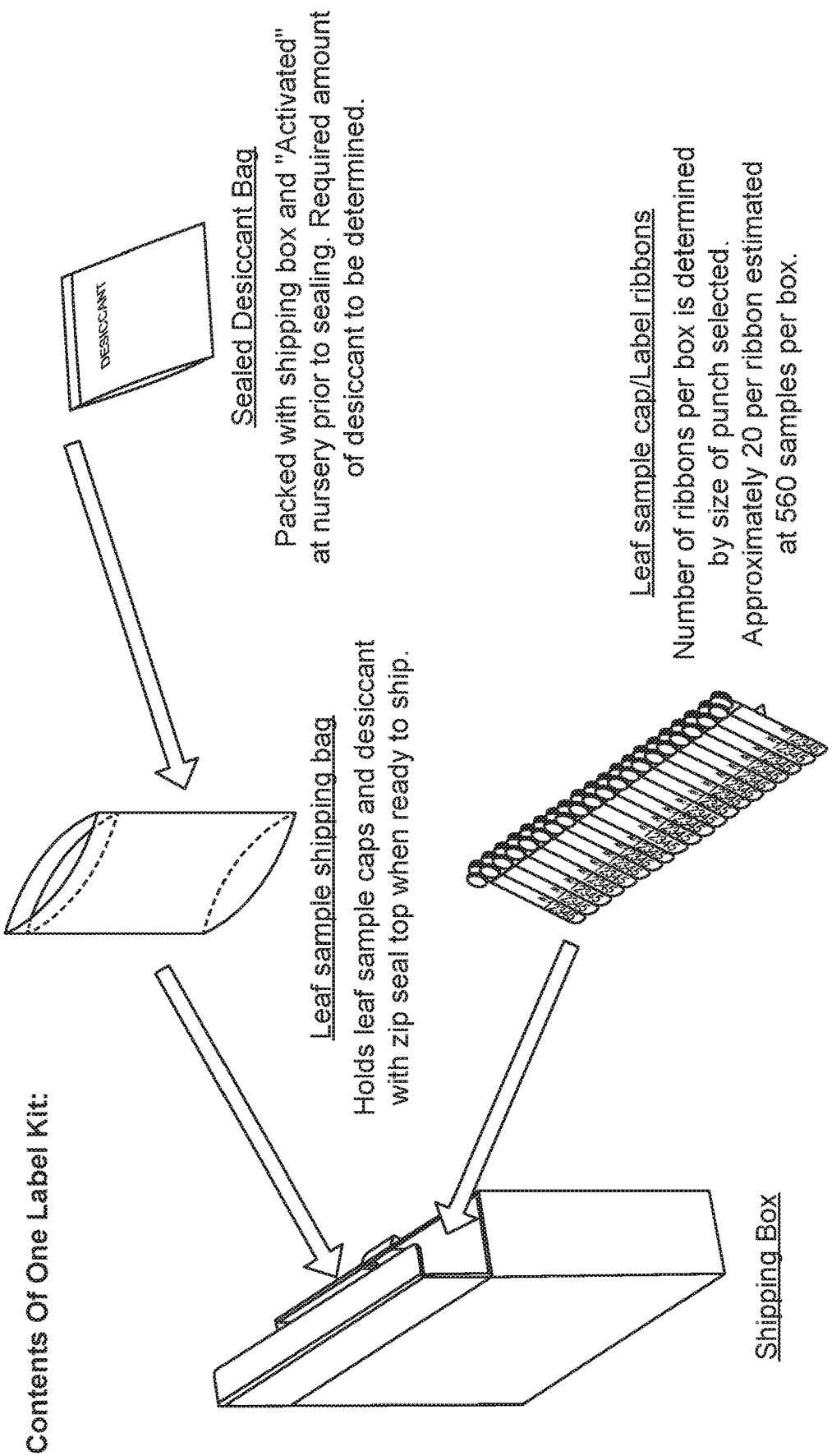
FIG. 7A depicts sampling device system, according to many embodiments of the invention.
Figure 7B:
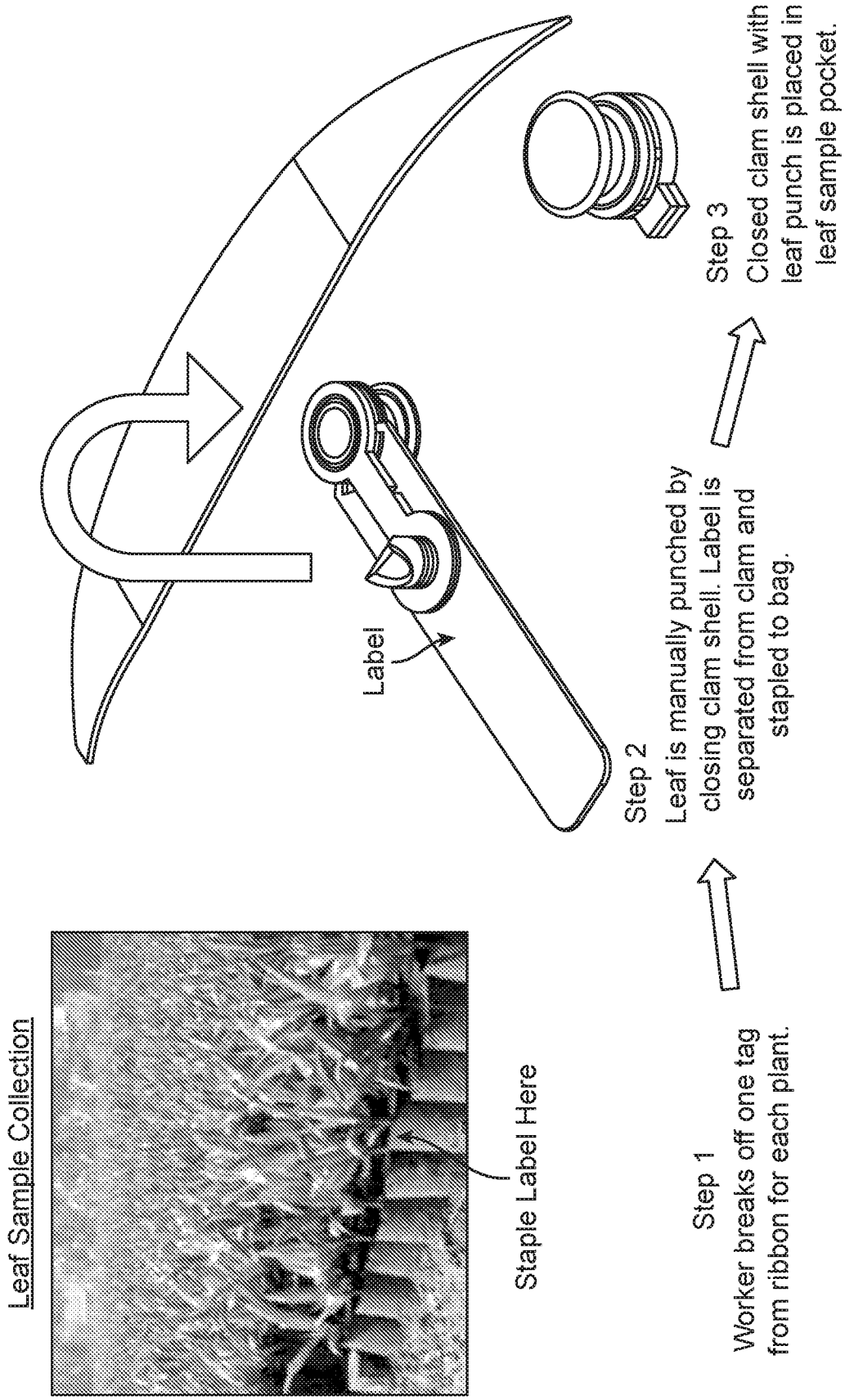
Figure 7C:
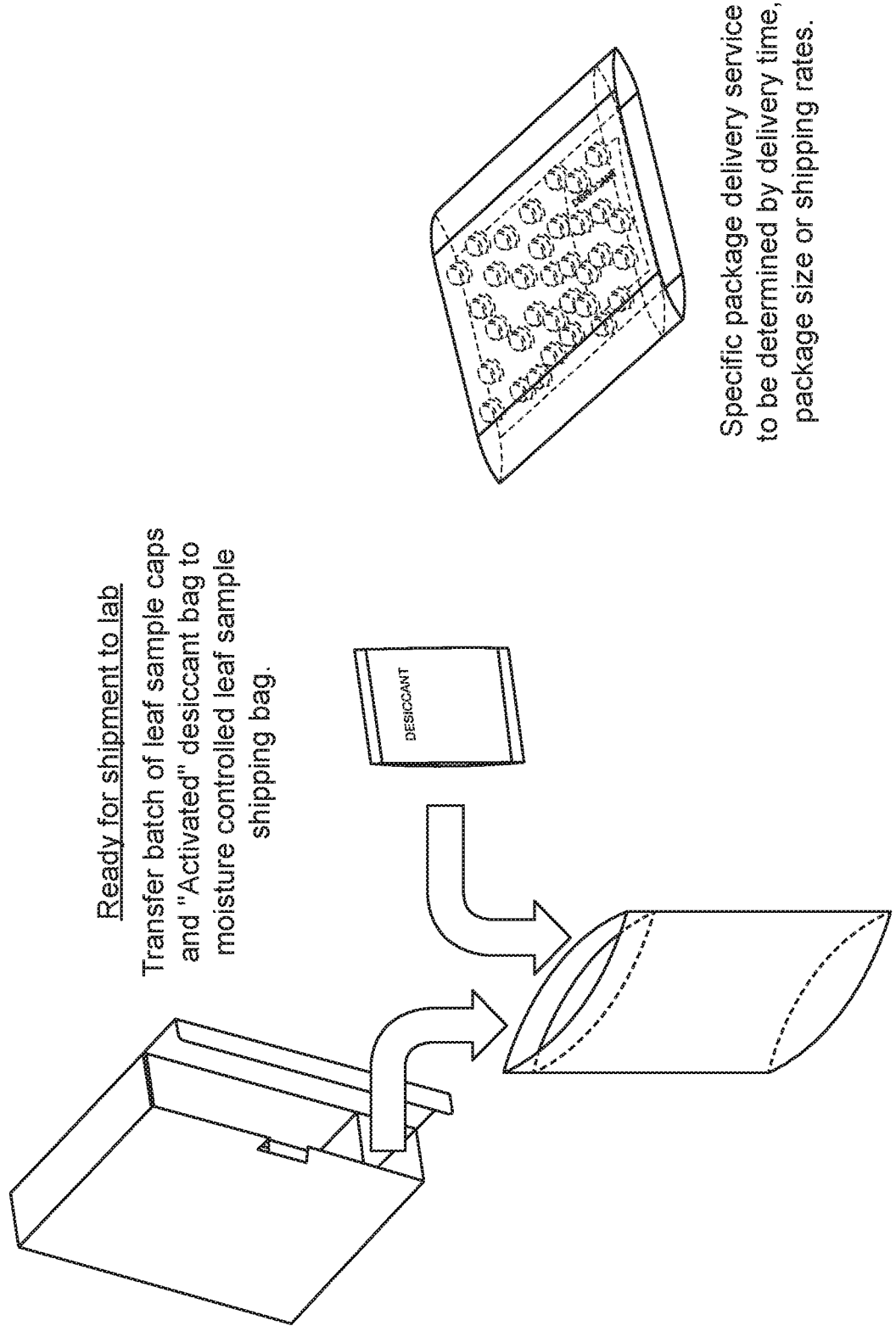

FIGS. 7A through 7C depict the contents of a sampling device kit and method for use of a sampling device. The contents of a kit can be provided within a shipping box, a sample shipping bag, a sealed descant bag, and a plurality of sampling devices, which, for example, can take the form of any of the sampling devices and combinations thereof disclosed herein. The amount of sampling devices can vary depending on the needs of a user, generally at least one sampling device is provided. The leaf sample shipping bag is configured to hold leaf samples and the sealed desiccant bag.

At FIG. 7B, the user detaches one rigid label of the plurality of labels from the strip provided in the kit. The resulting sampling device is then applied to a leaf as shown, by closing the cap of the sampling device over the lower portion, with a portion of the leaf lying in between. The resulting action causes a sample of the leaf to be securely deposited and immobilized within the sampling device. The label of the sampling device is detached and secured either to the plant directly, or indirectly the container holding the plant from which the sample was taken. Thus, the sample within the sampling device can be traced back to the labeled plant or plant container, because the sampling device includes a matching or linked identification. This process can be repeated for additional plants until all the sampling devices within the kit of FIG. 7A are loaded with sample material.

At FIG. 7C, the sampling devices are placed within the sample shipping bag along with an activated desiccant, which dehydrates the samples during shipping via the vents provided within the sampling devices. The filled shipping bag is then placed within a shipping box provided within the kit and shipped to a sample testing facility.

Figure 8:
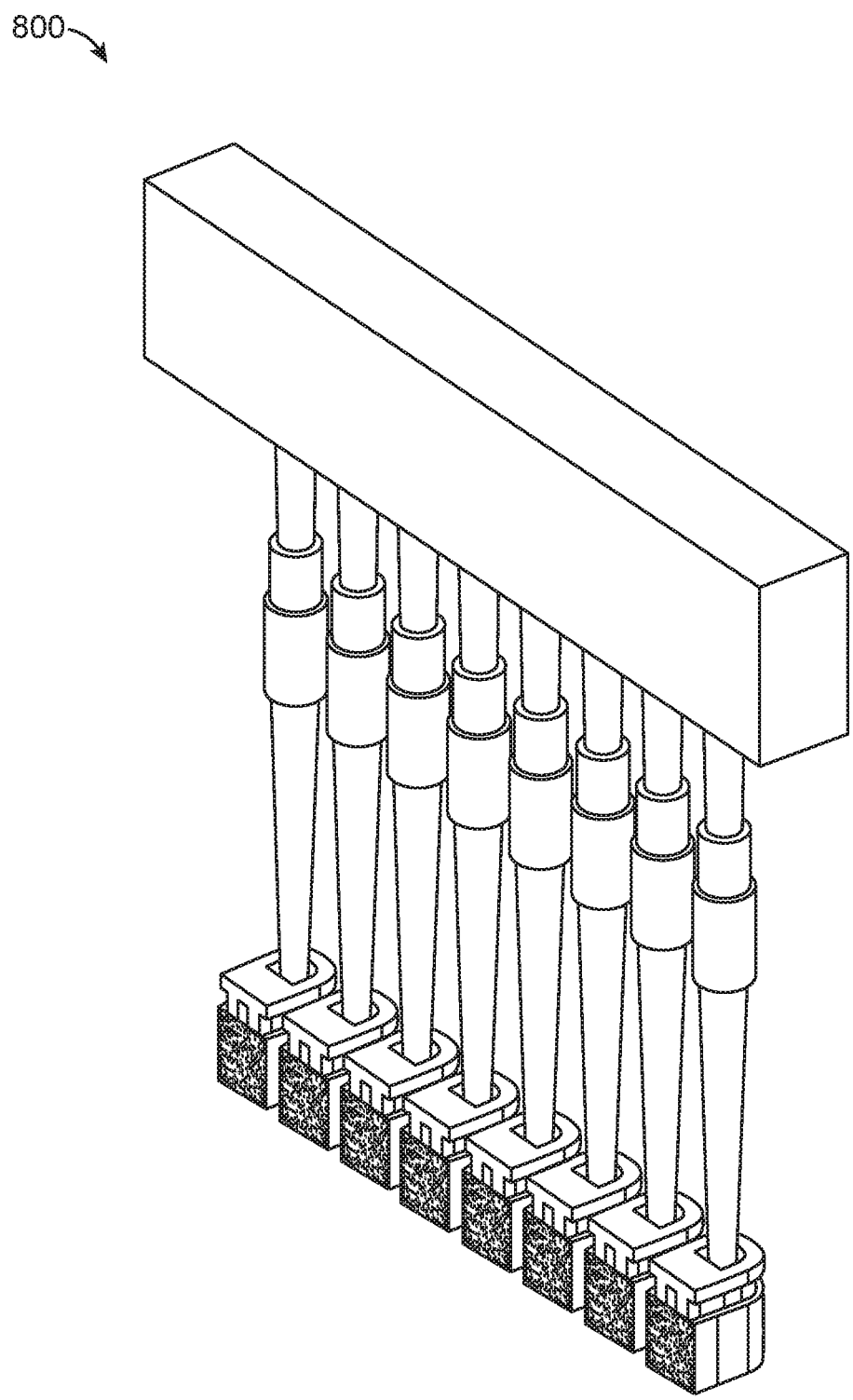

At FIG. 8, the shipping box along with its contents of the shipping bag filled with at least one sampling device are received and the sampling device is removed. The sampling devices and their contents can then be rehydrated with a solution (e.g. a plant tissue lysis buffer) by a filling apparatus 800 through the vents of the sampling devices, thus, preventing the need to open the sampling devices to test their contents. For example, reagents (e.g. an alkaline solution including but not limited to NaOH) for extracting nucleic acids or proteins can be added through the vents of the sampling devices. Exemplary protocols for nucleic acid extraction can be found in, e.g., Current Protocols in Molecular Biology (Ausubel et al., eds., 1994-1999). An assay (including but not limited to nucleic acid sequencing, polymerase chain reaction, etc.) can then be performed for each sample and the results of each assay can be correlated to particular plants by correlating the identification code of each sampling device to the remaining label left at the place of harvest.

Figure 9A:
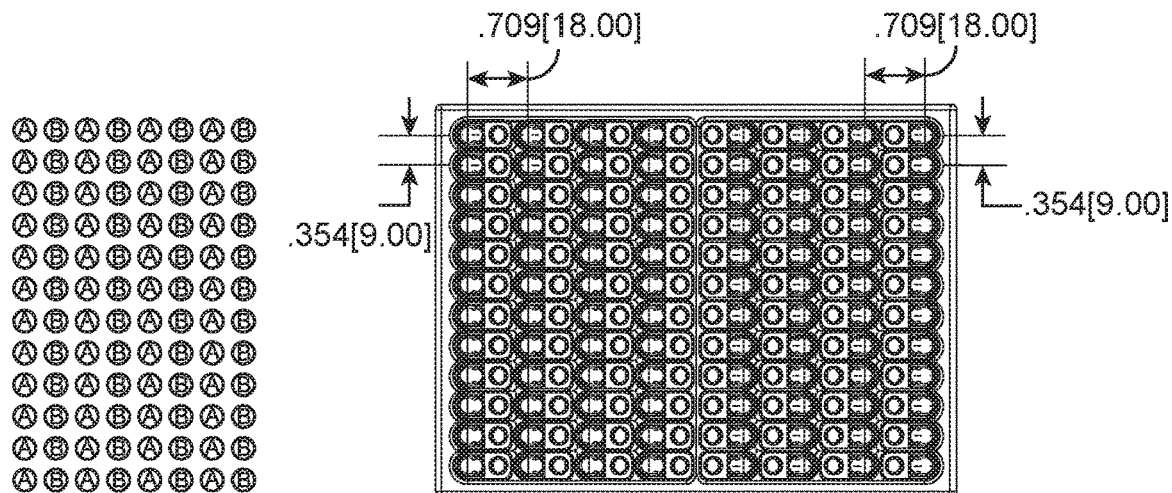
FIGS. 9A-9C show a method for processing an array of sampling devices, according to many embodiments of the invention.
Figure 9B:
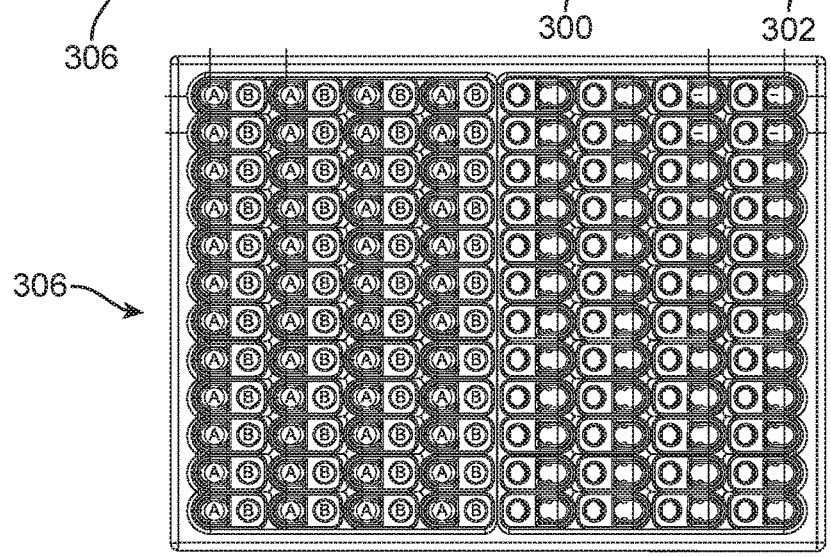
Figure 9C:
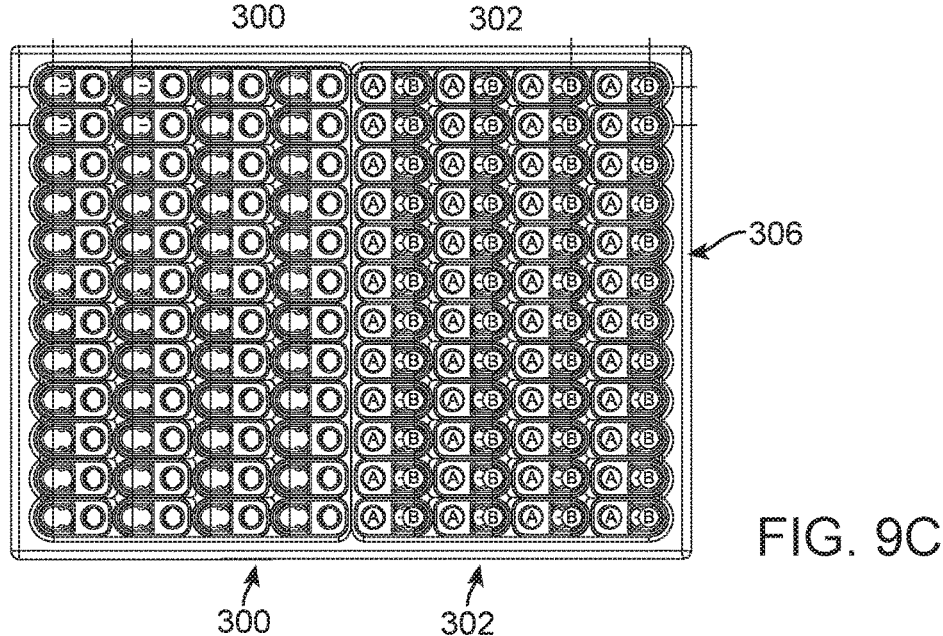

FIGS. 9A-9C show steps of a method for using the sampling device 230 of FIGS. 5C-5F. As noted above, the each interior passage 208 and opening 236 are placed at the theoretical well locations of a standardized 96 well microplate, and therefore arranged to be compatible with commercially available liquid robotic handling apparatuses configured for standardized microplates. However, because there is only one sample container per sampling device 230, only the interior passages (vents) 208 hold samples, while the openings 236 serve as passages into dead space. This arrangement provides compatibility with a standardized liquid handling machine, which provides a pipette for each standardized well location. If the openings 236 were not present, pipettes would otherwise collide due to the length of the sampling device 230.

At FIG. 9A, the sampling devices 230 are arranged into a first array 300 and a second array 302, with each array here containing 48 sampling devices 230 as shown at FIG. 5G. The sampling devices 230 of each array are arranged in an identical fashion, but the arrays mirror image one another such that the vents of each sampling device 230 of the first array 300 are placed on the left hand side, while the vents of each sampling device 230 of the second array 302 are placed on the right hand side. The first and second arrays are placed in adjacent to a pipette array 306, which has a standardized array of 96 pipettes, here shown in alternating rows of A and B pipettes. The pipette array 306 can be part of a commercially available liquid handling apparatus, such as the IntelliQube® by Douglas Scientific. Relative movement of the pipette array 306 and first and second arrays of sampling devices can be accomplished by robotic systems, as is known in the art, or in some cases semi-automatically derived by use of sliding sampling device holding fixtures utilizing bearing slides and a pipette array limited to vertical automated movement.

At FIG. 9B, the pipette array 306 is moved such that each pipette is placed into a dead space passage or vent of the sampling devices of the first array 300. Here, the A rows of pipettes are placed in fluid communication with the vents, and thus in fluid communication with the sample container portion of the sampling devices which contain leaf samples and have been prefilled with fluid, while the B rows of pipettes are positioned into the dead space passages. Fluid can then be withdrawn from the A rows of pipettes. In some cases, only the first array 300, or a lesser portion thereof, of sampling devices is present, and hence only half or less than half the pipette array 306 will be utilized.

At FIG. 9C, the pipette array 306 is moved such that each pipette is placed into a dead space passage or vent of the sampling devices of the second array 302. Here, due to the mirror image arrangement of the first array 300 and the second array 302, the B rows of pipettes are placed in fluid communication with the vents, and thus in communication with the sample container portion of the sampling devices which contain leaf samples and have been prefilled with fluid, while the A rows of pipettes, which were already utilized for the first array 300, are positioned into the dead space passages. Fluid can then be withdrawn from the B rows of pipettes. In this manner 96 samples can be processed from 96 sample containers.

Other variations are within the spirit of the present invention. Thus, while the invention is susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions, and equivalents falling within the spirit and scope of the invention, as defined in the appended claims.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A sampling device comprising:
   a lower portion comprising a sample container;
   a cap moveably attached with the lower portion and comprising a cutting edge configured for cutting a leaf, such that when the cap is attached to the lower portion with a leaf therebetween, a leaf sample is deposited into the sample container of the lower portion, the cap also comprising a dead space opening configured to receive a first pipette,
   wherein the cap is moveably attached to the lower portion by an elongated post extending out of the lower portion, and wherein the cap includes a vent in fluid communication with the sample container such that the leaf sample is dried during transport of the sampling device, the vent being configured to receive a second pipette.

2. The sampling device of claim 1, wherein the dead space opening and the vent are spaced 9 mm apart.

3. The sampling device of claim 1, wherein the sampling device is configured to be arranged in an array of similarly configured sampling devices.

4. The sampling device of claim 1, wherein the lower portion comprises an at least partially oval-shaped sample container.

5. The sampling device of claim 1, wherein a dead space passage is at least partially formed within the elongated post.

6. The sampling device of claim 1, wherein the cap comprises an elongated cutting post that extends into the sample container.

7. The sampling device of claim 6, wherein the elongated cutting post is configured to immobilize the leaf sample at a bottom portion of the sample container.

8. The sampling device of claim 7, wherein the bottom portion comprises a depth limiting wall for limiting ingress of the bottom portion over a leaf.

9. The sampling device of claim 1, further comprising a rigid label that extends in cantilever.

10. The sampling device of claim 1, wherein the vent is configured to act as a filling conduit for a sample preparation fluid.

11. A method for sampling a leaf of a plant using a sampling device system, the method comprising:
   obtaining a plurality of sampling devices as recited in claim 1;
   arranging the plurality of sampling devices in first and second sampling device arrays;
   positioning the plurality of sampling devices adjacent to an array of pipettes, the array of pipettes comprising a first plurality of pipettes and a second plurality of pipettes arranged in alternating rows;
   moving the array of pipettes such that the first plurality of pipettes move into the vents of the first sampling device array and the second plurality of pipettes lower into the dead space openings of the first sampling device array;
   withdrawing fluid from the vents of the first sampling device array using the first plurality of pipettes;
   moving the array of pipettes such that the first plurality of pipettes moving into the dead space openings of the second sampling device array and the second plurality of pipettes lower into the vents of the second sampling device array;
   withdrawing fluid from the vents of the second sampling device array using the second plurality of pipettes.

12. The method of claim 11, wherein the dead space opening and the vent are spaced 9 mm apart.

13. The method of claim 11, wherein the plurality of sampling devices arranged in a sampling device array are positioned to where the distance between the dead space opening and the vent of a first sampling device is the same as the distance between the vent of a first sampling device and the vent of a second sampling device in the array.

14. The method of claim 13, wherein the distance between the dead space opening and the vent of a first sampling device is 9 mm and the distance between the vent of a first sampling device in the array and the vent of a second sampling device in the array is also 9 mm.

15. The method of claim 11, wherein the first and second sampling array are arranged so as to be accessible by the same liquid handling device.

16. The method of claim 15, wherein the first sampling array directly abuts the second sampling array.

17. The method of claim 15, wherein the second sampling array is arranged as a mirror image of the first sampling array.

18. The method of claim 11, wherein the plurality of sampling devices comprises 96 sampling devices.

19. The sampling device of claim 9, wherein the rigid label extends from the lower portion of the sample container or an upper portion of the sample container, and is detachable therefrom.

* * * * *